United States Patent

[11] 4,071,558
[45] Jan. 31, 1978

Bentley

[54] AROMATIC POLYAMINES AND THEIR PREPARATION

[75] Inventor: Floyd E. Bentley, Austin, Tex.

[73] Assignee: Texaco Development Corporation, New York, N.Y.

[21] Appl. No.: 884,730

[22] Filed: Dec. 12, 1969

Related U.S. Application Data

[63] Continuation of Ser. No. 671,200, Sept. 28, 1967, abandoned, which is a continuation-in-part of Ser. No. 335,396, Jan. 2, 1964, abandoned, which is a continuation-in-part of Ser. No. 243,648, Dec. 10, 1962, abandoned.

[51] Int. Cl.$^2$ ............................................. C07C 85/24
[52] U.S. Cl. ........................... 260/570 D; 260/2.5 AT;
260/2.5 AQ; 260/77.5 AM; 260/453 AM;
260/453 PH
[58] Field of Search ..................................... 260/570 P

[56] References Cited

U.S. PATENT DOCUMENTS

| | | | |
|---|---|---|---|
| 2,511,748 | 6/1950 | Smith et al. | 260/570 X |
| 2,683,730 | 7/1954 | Seeger et al. | 260/453 |
| 2,818,433 | 12/1957 | Erickson | 260/570 |
| 2,950,263 | 8/1960 | Abbotson et al. | 260/2.5 |
| 2,974,168 | 3/1961 | Sharp et al. | 260/570 |

OTHER PUBLICATIONS

Houben-Weyl, "Methoden der Organischen Chemie", 4th ed., vol. 14/2, pp. 293–295 (1963).

*Primary Examiner*—Robert V. Hines
*Attorney, Agent, or Firm*—James L. Bailey

[57] ABSTRACT

A predetermined 2,4'-isomer content in a polyamine reaction mixture resulting from the aniline/formaldehyde condensation reaction can be achieved.

Aniline and formaldehyde can be condensed in the presence of solid acidic catalysts to form a mixture of the following amines:

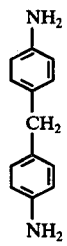

4,4'-diaminodiphenylmethane

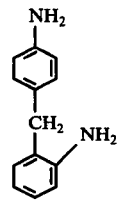

2,4'-diaminodiphenylmethane

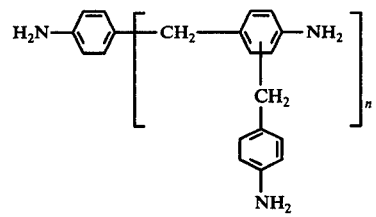

higher methylene polyphenylpolyamines where $n$ is an integer of from 1 to 3. The amount of 2,4'-isomer can be varied between 30 and 95 wt. % of the diamine component of the mixture by conducting the condensation reaction in the presence of an acid activated clay catalyst at a reaction temperature of about 80° to about 300° C. When the reaction is conducted in the presence of a silica-alumina cracking catalyst or a silica-magnesia catalyst, the 2,4'-isomer content can be varied from about 15 to about 50 wt. %. In using the latter class of catalyst it is possible to prevent formation of a secondary amine by conducting the condensation reaction at a lower temperature and then digesting at a temperature of from about 175° to about 220° C. for from about 1 to about 5 hours, depending upon the temperature used.

12 Claims, No Drawings

AROMATIC POLYAMINES AND THEIR PREPARATION

CROSS REFERENCES TO RELATED APPLICATIONS

This application is a continuation of my pending application Ser. No. 671,200 which was filed on Sept. 28, 1967 and now abandoned as a continuation-in-part of my then copending application Ser. No. 335,396, filed Jan. 2, 1964, entitled "Functional Polyaryl Compounds and the Preparation and Utilization Thereof," now abandoned, which in turn was a continuation-in-part of my then copending application Ser. No. 243,648, filed Dec. 10, 1962, entitled "Polyamine Preparation," now abandoned.

BACKGROUND OF THE INVENTION

1. Field of the Invention

The field of this invention relates to the production of aromatic amine precursors for the production of isocyanates for the manufacture of polyurethane foams. The isomeric distribution of the diamine portion of the aniline/formaldehyde reaction products can be predetermined through the practice of the method of my invention. By varying the proportions of diamine to polyamine and the isomeric distribution of the diamine component, properties such as viscosity and reactivity of the derived isocyanate can be predetermined and controlled.

2. Description of the Prior Art

The teachings of the prior art disclose the production of diaminodiphenylmethanes and polyaminopolyphenylmethanes for use as precursors in production of isocyanates for the manufacture of polyurethane foams. The method taught by the prior art involves the reaction of aniline with formaldehyde in the presence of a Lewis acid, preferably hydrochloric acid. In reacting in this manner the aniline forms the hydrochloride and then further reacts with the formaldehyde to form the polyphenylpolyamine.

In practicing this prior art method it is necessary to use corrosion resistant materials in the plant equipment, since the acid is added and then later neutralized through the addition of a strong base, usually sodium hydroxide. In addition, the prior art teaches that only a maximum of 10% of the 2,4'-isomer in the diamine portion of the reaction mixture is possible using this method of manufacture. While in some instances the product manufactured in this manner is satisfactory, a great deal is left to be desired because of the inherent lack of flexibility using this aniline hydrochloride method.

U.S. Pat. No. 2,683,730 teaches the condensation of aniline and formaldehyde in the presence of a hydrochloric acid catalyst to give a polyamine with up to 40 wt. % diamine content in the polyamine reaction product. U.S. Pat. No. 2,818,433 further amplifies the ability to vary the ratio of diamine to higher polyamines further increasing the diamine production and decreasing the production of the polyamine. This patent teaches that up to 10% of the 2,4'-isomer may be present in the reaction product as an impurity, but nowhere does the prior art teach my method of varying the production of the 2,4'-isomer in the diamine portion of the reaction

OBJECTS OF THIS INVENTION

Accordingly, it is an object of my invention to provide a method for varying the isomeric content of the diamine portion of the aniline and formaldehyde reaction product.

It is a further object to produce new mixtures of diaminodiphenylmethanes and polymethylene polyphenylpolyamines, suitable for conversion into the corresponding polyisocyanates by reaction with phosgene, wherein the proportions of 2,4'-diamine in the mixtures are increased and controlled within predetermined limits with the result that new polyisocyanates capable of forming new polyurethane plastics are obtained.

It is a further object of my invention to vary the content of the 2,4'-isomer diamine in the aniline/formaldehyde condensation reaction product to arrive at a predetermined isomeric distribution by reacting the aniline and formaldehyde in the presence of a solid acidic clay catalyst and adjusting the 2,4'-isomer content by regulating the final temperature at which the condensation reaction is performed.

It is a still further object of my invention to vary the isomeric content of the diamine to arrive at predetermined isomeric distribution by conducting an aniline and formaldehyde condensation reaction in the presence of a silica-alumina cracking catalyst or a silica-magnesia catalyst wherein the 2,4'-isomer content is determined by adjustment of the initial reaction temperature.

It is a still further object of my invention to abate the formation of secondary amines in the aniline/formaldehyde reaction in the presence of a solid acidic catalyst by employing a secondary or high temperature final heating step in the aniline/formaldehyde reaction process.

Other objects and advantages of my invention will become apparent to those skilled in the art in view of the following disclosures and examples and are intended to be included within the scope of my invention.

SUMMARY OF THE INVENTION

I have discovered methods for controlling between wide limits the isomeric content of the diamine proportion of the reaction product to arrive at a predetermined 2,4'-isomer content. By the use of my discoveries, I can vary the 2,4'-isomer content of the diamine portion from about 15 wt. % to about 95 wt. % of the diamine product. In the presence of a solid acidic clay catalyst, the 2,4'-isomer content is varied within the range 30 wt. % to about 95 wt. % through the adjustment of the final reaction temperature and conditions.

When the silica-alumina or silica-magnesia catalyst is used, the 2,4'-isomer content is varied within the range of 15 wt. % to about 50 wt. % by adjustment of the initial reaction temperature. When the method of my invention is used to vary the 2,4'-isomer content of the diamine portion of the reaction product, I have further discovered that a secondary amine condensation product is formed when the predominant reaction product is the higher polyamine. As a further improvement of my invention, I have discovered that this deleterious secondary amine reaction product can be removed by a further digestion step of the polyamines at elevated temperatures.

DESCRIPTION OF THE INVENTION

The New Compositions of the Invention

This invention relates to polyfunctional polyaryl compounds. More particularly, the present invention is directed to polyaminopolyphenylmethanes of a new isomer distribution, a method for the preparation of such polyamino compounds varying the isomeric distribution, the preparation of new polyisocyanate isomer mixtures therefrom and the production of polyurethanes from such polyisocyanates.

It has heretofore been proposed to react aniline with formaldehyde in the presence of a strong mineral acid, such as hydrochloric acid, whereby a reaction occurs between the corresponding aniline hydrochloride and formaldehyde to provide a reaction mixture which, on neutralization with a base, may be treated to recover mixtures of polyphenylamines composed principally of polyphenylamines having the following structural formulae:

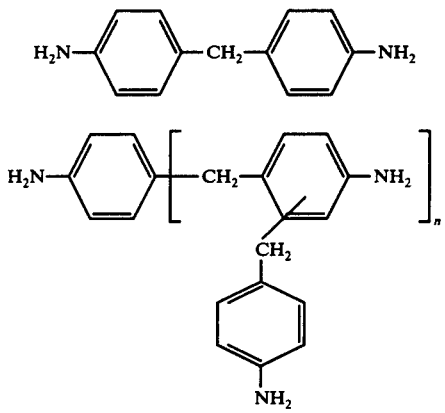

wherein $n$ is an integer having a value of 1 to 3 and normally has an average value of about 1.

Although the results obtained have been satisfactory as shown in U.S. Pat. Nos. 2,818,433 and 2,683,730, for example, in the sense that the above-indicated products can be formed, the process has left much to be desired. For example, it is necessary to utilize large quantities of both a mineral acid and a base which adversely affect the economics of the process and also the ease of conducting the reaction. In addition, the use of large quantities of mineral acids and bases presents a severe corrosion problem. Still further, the principal diaminodiphenylmethane that is formed is 4,4'-diaminodiphenylmethane. It has not been known heretofore how to prepare more than 10 wt. % of the 2,4'-diaminodiphenylmethane, much less a method for selectively varying the isomeric distribution to arrive at a predetermined 2,4'-isomer content. As a consequence, when a diaminodiarylmethane reaction product prepared in the conventional manner is converted to a diisocyanatodiphenylmethane reaction product, the diisocyanate product will have a comparatively high melting point and often an undesirably high reactivity. As a consequence, it is normally necessary to use a prepolymer when polyurethanes are to be prepared from a conventional product composed primarily of 4,4'-diisocyanate (i.e., by initially reacting the diisocyanate with a limited quantity of a hydroxy-terminated polyether or polyester to provide an isocyanato-containing prepolymer). The prepolymer is then reacted with an additional amount of hydroxy-terminated polyester or polyether to provide a polyurethane.

The foregoing and other shortcomings are overcome in accordance with the present invention, which provides new mixtures of 2,4'-diaminodiphenylmethane with 4,4'-diaminodiphenylmethane and, in particular, mixtures containing from about 15-20 wt. % to about 95 wt. % of the 2,4'-isomer and, correspondingly, from about 80-85 wt. % to about 5 wt. % of the 4,4'-isomer. These mixtures may be converted to the corresponding isocyanates to provide new mixtures of isocyanates that are liquid and are of particular utility in the preparation of polyurethane reaction products such as polyurethane elastomers and polyurethane foams, for example.

Producing The New Compositions

The process of the present invention may be briefly described as a process wherein formaldehyde or a polymer thereof is brought into reactive contact with aniline in the presence of a solid acidic catalyst whereby a reaction mixture is formed which is composed principally of diaminodiphenylmethane and higher molecular weight condensation polymers of the formaldehyde and the aniline. The reaction conditions are such that the products of the reaction, as indicated, will have an isomer distribution which is significantly different from the isomer distribution obtained by the use of a strong mineral acid. For example, the reaction product of the present invention may comprise dimers and higher molecular weight condensation products, such dimers having the following formulae:

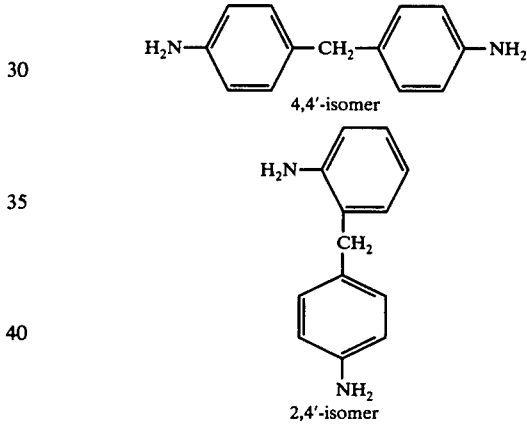

Thus, in accordance with the present invention, it is possible to obtain a mixture of 2,4'-diaminodiphenylmethane with 4,4'-diaminodiphenylmethane containing from about 15 wt. % to about 95 wt. % of the 2,4'-isomer (and preferably, about 30 wt. % to 95 wt. %).

The catalyst to be employed in accordance with the present invention may be generically defined as a solid acidic siliceous catalyst, such as acid-activated siliceous clays, silica-alumina cracking catalyst and silica-magnesia catalyst, for example. However, more basic materials such as, for example, tungsten oxide, vanadium and titanium oxide are not effective catalysts for the reaction.

A silica-alumina cracking catalyst containing 5 wt. % to 30 wt. % of alumina gives superior results not obtainable with other members of the genus.

As pointed out above, the use of solid catalysts in the aniline/formaldehyde condensation leads to a new mixture of controlled isomer content. The actual distribution between the 2,4'- and the 4,4'-forms can be regulated by readily controlled variables, including temperature, choice of catalysts and method of addition of reactants. Thus, with an acid activated clay catalyst such as Superfiltrol clay, I have fond that the 2,4'-isomer content varies with reaction temperatures from about 30 wt. % at 80° C. to 95 wt. % at 250° C. For example, the 2,4'-isomer content will be about 70 wt. % if the final temperature of the reaction is 175° C. and about 80 wt. % if the final temperature of the reaction is 200° C.

On the other hand, with a synthetic silica-alumina cracking catalyst, I have found that the 2,4° -isomer content ranges from about 15 wt. % to about 50 wt. % and is insensitive to temperature variation after the aniline/formaldehyde reaction begins. Therefore, when higher 2,4'-diamine content is desired, the acid activated clay catalyst is employed with a high final reaction temperature. When a lower 2,4'-diamine content is desired, the preferred catalyst is the synthetic silica-alumina cracking catalyst.

It is apparent, therefore, from the above discussion that compositions having a predetermined content within a relatively wide range of isomer distribution may be prepared by the methods of this invention. Derivatives of these compositions, such as the diisocyanates, will reflect the same isomeric distribution.

The molar ratio of aniline to formaldehyde may be varied within comparatively wide limits. Thus, for example, from about 1 to about 10 mols of aniline may be employed per mol of formaldehyde. In general, at the lower aniline: HCHO ratios, such as ratios of from about 1:1 to about 2.5:1, the higher polymers will be formed preferentially and the yield of higher polymers is in excess of the yield of dimer. However, as progressively larger amounts of aniline are used, the yield of dimer is progressively increased at the expense of polymer yield. Thus, with aniline to formaldehyde ratios of from about 3:1 to about 10:1 or more, the reaction product will be composed primarily of the dimer. A range of ratios of aniline to formaldehyde which gives good flexibility in determining a desired diamine to higher polyamine ratios is from about 1:1 to about 4:1. As indicated above, the dimer will be formed as a mixture of the 2,4'- and 4,4'-diamine isomers.

Formaldehyde may be employed in any of its commercially available forms. Thus, aqueous solutions of formaldehyde called formalin, paraformaldehyde and "stabilized" methanol solutions of formaldehyde, for example, may be employed. One particularly preferred formaldehyde source is 37% formalin stabilized with about 12% methanol and containing about 51% water.

The reaction products will also include the water formed by the condensation reaction of the aniline and formaldehyde. In addition, there will be water added when formalin is used as the source formaldehyde, but the amount added will, of course, vary with the amount of methanol inhibitor, if any, in the formalin. The usual commercial formalin used for this reaction contains about 12 wt. % to 15 wt. % methanol.

Therefore, an aniline to water weight ratio is established depending upon the aniline/formaldehyde ratio and the form of the formaldehyde-producing product employed in the reaction. This aniline to water weight ratio has been found to vary from about 1.5:1 when uninhibited formalin solutions are used to about 40:1 when paraformaldehyde is used to provide the formaldehyde for the reaction; the weight ratio of aniline to water also being from about 4:1 to about 40:1 in many instances. However, since the aniline to water limits are not critical to the practice of my invention, it is possible to operate successfully outside these limits if it is so desired. It may be desirable to operate while continuously removing water from the reaction mixture. This mode of operation is also within the scope of my invention and in such cases the aniline to water weight ratio becomes quite high.

The reaction may be conducted in the presence or absence of a solvent. When a solvent is to be employed, it may be any of the conventionally known hydrocarbon solvents or chlorinated hydrocarbons, such as aromatic or aliphatic solvents boiling within the range from about 100° to about 200° C. The solvent should be employed in an amount sufficient to provide a single phase solution of the amine compound.

The reaction conditions to be employed may suitably include a reaction temperature within the range of about 80° to about 300° C., and more preferably within the range of about 120° to about 200° C. The reaction appears to proceed most smoothly with aniline at a temperature within the range of about 125° to about 130° C. when an acid-activated clay, such as Superfiltrol clay, is used as catalyst and about 140° to 200° C. when a silica-alumina catalyst is used. The influence of temperature on isomeric distribution has already been discussed.

Pressure is not particularly critical with respect to the process. However, the pressure should be sufficient to provide for liquid phase reaction conditions.

The reaction proceeds smoothly under the above-described conditions and is normally substantially complete upon addition of the formaldehyde. However, because of the exothermic nature of the reaction, it is normally preferable to add the formaldehyde at a rate such that the desired reaction temperature can be maintained. It is normally possible to bring the reaction to complete within from about five minutes to about one hour in conventional equipment.

The polyaminopolyphenylmethanes of the present invention are recovered from the reaction mixture by any desired means. They are conveniently recovered by filtering the catalyst and removing water and excess aniline under reduced pressure. The bottoms from these operations will consist of diamine and polyamine in proportions depending on the ratio of aniline to formaldehyde, as indicated above. If it is desired to separate the diamine from the polyamine, that is easily accomplished by simple distillation whereby the diamine is flashed from the nonvolatile polyamine residue. The overhead product may be removed, for example, at from about 170° to about 200° C. at about 0.5 to about 0.025 mm. Hg pressure and will consist essentially of diaminodiphenylmethane containing from about 15 wt. % to about 95 wt. % of 2,4'-diaminodiphenylmethane and, correspondingly, from about 85 wt. % to about 5 wt. % of 4,4'-diaminodiphenylmethane.

The dimer and higher products of the present invention are useful for a variety of purposes. For example, they may be utilized as raw materials for the production of the corresponding polyisocyanates.

The thus-prepared polyamines may be converted to the corresponding polyisocyanates in any desired manner. Thus, conventional phosgenation techniques may be employed. If desired, an improved phosgenation process as disclosed in Rowton U.S. Pat. No. 3,344,162, entitled "Polyisocyanate Production," may be employed. Phosgenation may be conducted either on a continuous basis or on a batch basis.

Eliminating Secondary Amine Formation

It has been noted that some of the polyisocyanates produced from the polyamines of my invention have higher viscosities and higher hydrolyzable chlorine content when made from the amine reaction product which is predominantly the polyamine as opposed to the diamine. When the amine reaction product is predominantly the diamine, the resulting diisocyanates do not exhibit this higher hydrolyzable chloride and viscosity as found when the polyisocyanate product is produced from the polyamine precursor which has a low diamine content.

I have discovered, however, as a further improvement of the process of contacting aniline and formaldehyde in the presence of a solid acidic catalyst that this high viscosity and high hydrolyzable chloride content can be avoided by heating the crude polyamine mixture in the presence of the solid acidic catalyst at a temperature higher than that required for the condensation reaction, usually 175° to 200° C. For example, I have found that 140° C. is a convenient temperature for the condensation reaction in the presence of a silica-alumina catalyst when the aniline, formaldehyde and catalyst were premixed and heated to the reaction temperature. However, when the reaction is conducted at this temperature, there remains an intermediate condensation product which contains secondary amines. When these secondary amines are phosgenated they form not isocyanates but N,N-disubstituted carbamoyl chlorides which are structurally incapable of becoming isocyanate groups. This results in a high hydrolyzable chloride analysis and a consequent high viscosity. The presence of this carbamoyl chloride has been analytically determined by the infrared absorbence at the $5.75\mu$ wave length.

I have discovered a way to substantially eliminate the problem of secondary amine formation in the condensation reaction catalyzed by the silica-alumina or silica-magnesia catalyst. This is accomplished by digesting the polyamine mixture in the presence of the catalyst at a higher temperature of about 175° to about 200° C. for one to five hours. The product obtained by subsequent phosgenation has considerably reduced viscosity and a lower still perceptible hydrolyzable chloride content as shown by slight infrared absorption at the $5.75\mu$ wave length. Since I discovered that the secondary amines are preferably formed at lower temperatures, a further reduction in the secondary amine content can be achieved by adding the formaldehyde to a hot mixture of aniline and solid acidic catalyst.

It will also be observed from some of the following examples that the viscosity and hydrolyzable chloride problems that result from the presence of secondary amines do not arise when the diisocyanate has been distilled from the polyisocyanate phosgenation reaction product. In addition, this is also true when the isocyanate is produced from diamines distilled from the aniline/formaldehyde reaction products.

Effect of Catalyst Selection

When an activated acid clay such as Superfiltrol acid clay is the catalyst, the 4,4′-isomer of a diaminodiphenylmethane is rearranged fairly rapidly to the 2,4′-isomer. Thus, the distribution between the 4,4′-and the 2,4′-isomer is largely a function of the final temperature. However, when it is desired to reduce the content of the 2,4′-isomer in the diamine compnent, the silica-alumina cracking catalyst or silica-magnesia catalyst is used and the isomer distribution is determined largely by the initial reaction temperature, there being little additional change in the 2,4′-isomer content if the temperature is subsequently raised in the presence of the catalysts. Thus, in the practice of my invention, if it is desired to have a high 2,4′-isomer content, that is, between 30 and 95 wt.%, the acid activated clay should be used as a catalyst and the temperature adjusted as hereinbefore described.

If a lower 2,4′-diamine content is desired, the silica-alumina or silica-magnesium catalyst is used. Since the initial temperature determines the 2,4′-isomer content with these catalysts, the aniline and formaldehyde and catalyst can be premixed at ambient temperatures and then raised to its reaction temperature determined by the desired 2,4′-isomer content as hereinbefore disclosed. When the reaction is performed at lower temperatures, such as between 80° and 150° C., there will be the formation of the undesired reaction products, including the secondary amines, that has been described above. To overcome this problem, after the reaction is completed the temperature is raised to the range of from about 175° to about 200° C. to digest the reaction products for an appropriate period of time, usually from about 1 to about 5 hours to cause the secondary amine reaction product to rearrange into the desired polyamine product. Examples XVII to XXIII are illustrative and further descriptive of this aspect of my invention.

Production of New Isocyanate Mixtures

In view of the variation in composition of the starting polyphenylpolyamine that is possible by changing either or both of the dimer-polymer ratio and the 2,4′-diamine and 4,4′-diamine isomer ratios, it is apparent that the corresponding polyisocyanates of this invention will also reflect the structural features. However, it has been discovered that it is the presence of the substantial proportions of the 2,4′-diisocyanate isomer which is responsible for the novel characteristics of the polyisocyanates prepared from the new polyamine compositions of the present invention. Thus, whether the isocyanate is used as a distilled material or as a crude mixture, it is the influence of the 2,4′-isomer that is essential.

When the diaminodiphenylmethane mixture is phosgenated to provide a diisocyanate, the dimer content may vary from about 20 to about 100 wt.%. The latter value is obtained in the case of distilled isocyanates or crude isocyanates from distilled diamine. More usually, however, a range of 40 to 85% is preferred in order that the isocyanate product will have a functionality in excess of two.

Likewise, the 2,4′-isomer content may be varied over a wide range by selecting the corresponding amine prepared and described above. It has been found that, in contrast to pure 4,4′-diphenylmethane diisocyanate, which is a crystalline solid at room temperature, the mixture of diisocyanate isomers containing at least 25 wt.% of the 2,4′-isomer is a mobile liquid at room temperature. The liquid diisocyanate is processed, handled, or used more easily then the crystalline solid 4,4′-isomer. Therefore, an especially preferred range of 2,4′-isomer content of the diamine is from 25 to about 95 wt.%.

Another influence of the 2,4′-isomer is to moderate the reactivity of the polyisocyanate. Thus, in accordance with the present invention, it is possible to utilize the so-called "one-shot" technique in preparing rigid urethane foams from the novel isocyanate mixtures of the present invention.

The invention will be further illustrated by the following specific examples, which are given by way of illustration and not as limitations on the scope of this invention. Recent refinements in analytical techniques reveal that up to about 20% of what has been believed to be solely the 2,4'-isomer is 2,2'-isomer. Accordingly, it is intended that the 2,4'-isomer content should be construed to include any 2,2'-isomer may be present.

EXAMPLE I

In a three-necked flask equipped with mechanical stirrer, thermometer, reflux condenser, nitrogen inlet tube and additional funnel, were placed 280 g. of aniline (three mols) and 28 g. of Superfiltrol acid-washed clay catalyst. The system was swept with a slow stream of nitrogen and the temperature was raised to 125° to 130° C. Forty-one grams of formalin solution (37% by weight HCHO, 0.5 mol) was added during 30 minutes and water was removed continuously by means of a Dean-Stark type trap. The temperature of the reaction mixture was maintained at 125° C. for an additional 30 minutes and then the catalyst was removed by filtration.

Distillation of the filtrate at reduced pressure gave 177 g. of unreacted aniline and 96 g. of residue, which was light yellow in color. This residue on distillation at 0.05 mm. Hg gave 81 g. (84% yield) of material boiling at 175° to 185° C. which solidified to a white crystalline product (the diaminodiphenylmethane) and 14 g. of non-volatile residue (higher molecular weight aniline-HCHO condensation products).

The product had a neutral equivalent of 101 (calculated for the diaminodiphenylmethanes, 99) and melted at 66° C. An infrared analysis of the product showed that it contained 41% of the 2,4'-isomer.

EXAMPLE II

The experiment of Example I was repeated except one-half as much catalyst was used and the reaction temperature was kept at 150° to 160° C.

Distillation of the mixture gave 174 g. unreacted aniline, 83 g. diaminodiphenylmethanes and 13 g. of non-volatile polymeric aniline/formaldehyde condensation products. The diaminodiphenylmethanes contained 58% of the 2,4'-isomer, according to quantitative infrared analysis.

EXAMPLE III

The experiment of Example I was repeated except one-half as much catalyst was used and the temperature was maintained at 100° C. On distillation of the reaction mixture, there was obtained 205 g. of unreacted aniline, 44 g. of diaminodiphenylmethanes and 34 g. of nonvolatile residue. The diamine thus obtained contained 32% by weight of the 2,4'-isomer and 68% by weight of the 4,4'-isomer.

EXAMPLE IV

A one-gallon, stainless steel, stirred autoclave was charged with 3,350 g. of aniline (36 mols) and 168 g. of Superfiltrol clay, flushed with nitrogen and heated to 250° C. Over a 2-hour period was added 675 ml. of aqueous formalin solution (37% HCHO = 9 mols) and the reaction mixture was heated for 1 hour longer. The catalyst was filtered, water and excess aniline were removed by distillation at reduced pressure. The resulting residue was further distilled at low pressure and found to consist of 67% of diaminodiphenylmethane and 33% of higher molecular weight condensation products. The diamine was found by quantitative infrared analysis to consist of 94% of the 2,4'-isomer and 6% of the 4,4'-isomer.

EXAMPLE V

In the equipment described in Example IV was charged 3,350 g. of aniline (36 mols) and 168 g. of Superfiltrol clay, flushed with nitrogen and heated to 80° C. Over a 3-hour period was added 675 ml. of aqueous formalin solution (37% HCHO = 9 mols) and the reaction mixture was heated for three hours longer. The catalyst was filtered, water and excess aniline were removed by distillation at reduced pressure. The resulting residue was further distilled at low pressure and found to consist of 41% of diaminodiphenylmethane and 59% of higher molecular weight condensation products. The diamine was found by quantitative infrared analysis to consist of 34.5% of the 2,4'-isomer and 65.5% of the 4,4'-isomer.

Examples IV and V illustrate the wide variance possible in the practice of my invention using the same proportions of reactants but varying the temperature and time of the reaction in the presence of the acid activated (Superfiltrol) clay.

EXAMPLE VI

When 558 g. of aniline (6 mols) and 33 g. of flake paraformaldehyde (91% HCHO = 1 mol) were reacted in the presence of 28 g. of silica-magnesia fluidized cracking catalyst, work-up of the product provided 359 g. of excess aniline and 200 g. of residue (100% yield). The residue was found by vacuum distillation to consist of 87% diaminodiphenylmethanes and 13% of higher molecular weight aniline/formaldehyde condensation products. The diamine comprised 22% of the 2,4'-isomer and 78% of the 4,4'-isomer as determined by quantitative infrared analysis.

EXAMPLE VII

In the equipment described in Example I were placed 186 g. of aniline (2 mols) and 10 g. of Superfiltrol acid clay catalyst. The mixture was heated to 125° to 130° C. under a nitrogen sweep and 81 g. of formalin (1 mol HCHO) was added over a 1-hour period. The reaction was continued for ½ hour after completion of addition of formalin. The catalyst was then filtered from the hot mixture.

Distillation gave 41 g. unreacted aniline 73 g. volatile diamine and 71 g. nonvolatile polymers.

This experiment illustrates that a 2:1 mol ratio of aniline to formaldehyde can be used conveniently with a solid catalyst to yield a product containing an increased proportion of polyamines.

EXAMPLE VIII

The experiment of Example VII was repeated except a mol ratio of 1.35:1 of aniline to formaldehyde was used. It was necessary to add a solvent (o-dichlorobenzene) in order to maintain a fluid system so that catalyst could be filtered.

The mixture was distilled at reduced pressure to remove solvent and unreacted aniline. The residue, weighing 152 g., was further fractionated at 0.5 mm. Hg to give 20 g. volatile diamine and 130 g. nonvolatile polyamines.

EXAMPLE IX

A 1-gallon, stainless steel, stirred autoclave was charged with 1,256 g. of aniline (13.5 mols) and 62 g. of fluidized silica-alumina cracking catalyst. The autoclave was flushed with nitrogen and heated to 200° C. Over a 2-hour period, 450 ml. of aqueous formalin solution (37% HCHO = 6 mols) was added. Heating was continued at 200° C. for 2 hours after addition of formalin. The catalyst was filtered and water and excess aniline were removed from the filtrate by distillation at reduced pressure. There was obtained 911 g. of residue consisting of 43.3% diaminodiphenylmethane and 56.7% of higher molecular weight aniline/formaldehyde condensation products. The diamine contained 37% of the 2,4'-isomer and 63% of the 4,4'-isomer.

This example illustrates a preferred embodiment of the invention for preparation of a polyamine containing substantial amounts of higher molecular weight condensation products.

EXAMPLE X

Four hundred sixty-five grams of aniline (5 mols) was contacted with 68 g. of 37% formalin solution (0.83 mol HCHO) in a nitrogen atmosphere at 150° C. in the presence of 24 g. of vanadium oxide catalyst.

After 1 hour the catalyst was filtered from the reaction mixture and the filtrate was distilled at reduced pressure, giving 333 g. of aniline (3.58 mols) and 90 g. of a nonvolatile polymeric residue.

This example shows that a typical transition metal oxide, vanadium oxide, is unsatisfactory as a catalyst for forming diaminodiphenylmethane.

EXAMPLE XI

The polyamine phosgenated in this example was prepared by adding 37% aqueous formalin to a mixture of aniline and Superfiltrol activated clay at 130° C. (aniline: HCHO molar ratio, 6:1) as in Example I. The product contained 89% diamine of which 47% was the 2,4'-isomer.

A solution of 200 g. of the above polyamine in 1,200 g. of monochlorobenzene was run into a solution of 350 g. of phosgene dissolved in 1,900 g. of monochlorobenzene while maintaining the temperature at 25° to 30° C. The resulting slurry was heated rapidly to 110° C. to 120° C. while passing a slow stream of phosgene through the reaction mixture. When there was no longer any solid material in the flask, the reaction was halted. A total of 650 g. of phosgene had been used. Excess phosgene was removed with a stream of dry nitrogen and solvent was removed by flash evaporation.

The residue weighed 248 g. (theory 250 g.) and was a dark, fairly fluid liquid with the following properties:

| —NCO content | 7.58 meq./g. (theory 8.0) |
|---|---|
| Hydrolyzable Cl | 0.28 |
| Viscosity, cps. at 25° C. | 35 |

EXAMPLE XII

The amine to be phosgenated in this example was a distilled diamine prepared over Superfiltrol clay and containing 34.8 wt. % of the 2,4'-isomer.

Phosgenation of 200 g. of this diamine yielded 250 g. of a light-colored liquid diisocyanate with the following properties:

| —NCO content | 7.96 meq./g. (theory 8.0) |
|---|---|
| Hydrolyzable Cl | 0.31% |

EXAMPLE XIII

A crude diisocyanate was prepared from a distilled diamine containing approximately 50 wt. % of the 2,4'-isomer of diaminodipheylmethane. Four hundred grams of the crude diisocyanate was flash distilled at ~0.5 mm. Hg. The volatile distillate weighed 315 g. and was a light yellow, low viscosity material which remained liquid at room temperature. The following physical properties were observed.

| —NCO content | 7.98 meq./g. (theory 8.0) |
|---|---|
| n(25/D) | 1.6011 |
| d(20/20) | 1.2061 |
| Hydrolyzable Cl | 0.06% |

An infrared spectrum showed a high 2,4'-isomer content, as indicated by a strong absorption band at 13.2μ.

I have further discovered that the hydrolyzable chloride content of higher polyisocyanates is reduced when the final temperature of the aniline/formaldehyde condensation reaction is held between 175° and 200° C. for a period of time of from about 1 to about 5 hours, depending upon the temperature, during the condensation reaction. The following examples illustrate this aspect of my invention.

EXAMPLE XIV

The polyamine phosgenated in this example was prepared by reacting 37% aqueous formalin with aniline in the presence of a silica-alumina catalyst (aniline:HCHO molar ratio, 2.25:1) at 200° C. The polyamine contained 43.3% dimer of which 37% was the 2,4'-isomer. A solution of 200 g. of this polyamine in 1,400 g. monochlorobenzene was run into a solution of 400 g. phosgene dissolved in 1,600 g. monochlorobenzene while maintaining the temperature at 25° to 30° C. The resulting slurry was further phosgenated as described in Example XI, yielding 246 g. product polyisocyanate.

| —NCO content | 7.72 meq./g. (theory 8.0) |
|---|---|
| Hydrolyzable Cl | 0.85% |
| Viscosity, cps. 25° C. | 231 |

EXAMPLE XV

The polyamine to be phosgenated in this example was prepared by the condensation of aniline and paraformaldehyde at a molar ratio of 2.5:1 and at 175° C. for 5 hours over a silica-alumina catalyst. The product contained 61 wt. % dimer of which 22.5% was the 2,4'-isomer.

The phosgenation of 200 g. of this polyamine was performed as in Example XI, yielding 248 g. of a fairly light-colored, crude polyisocyanate with the following properties:

| —NCO content | 7.72 meq./g. (theory 8.0) |
|---|---|
| Hydrolyzable Cl | 0.41% |
| Viscosity, cps. at 25° C. | 53 |

EXAMPLE XVI

A rigid polyurethane foam was prepared from the polyisocyanate described in Example XV using the following formulations (parts by weight): 194 parts of crude isocyanate, 192 parts of Tetrol MG-525 (a polyoxypropylene polyol based on methyl-glucoside), 64 parts of Freon 11, 4 parts of silicone oil and 1.5 parts of 2-methyl-(2.2.2)diazabicyclooctane. The following properties were found:

| | |
|---|---|
| Cream time, sec. | 40 |
| Rise time, sec. | 150 |
| Tack-free time, sec. | 150 |
| Density, lb./ft.$^3$ | 1.91 |
| Compressive strength, psi. | 26.58 |
| Tensile strength, psi. | 52.3 |
| Heat distortion temp., ° C. | 172.0 |

| Dimensional stability | |
|---|---|
| 158° F., 100% R.H. | |
| 12 hours, % vol. change | +2.33 |
| % wt. change | −1.26 |
| 24 hours, % vol. change | +3.55 |
| % wt. change | −0.75 |
| 1 week, % vol. change | +5.38 |
| % wt. change | −1.76 |
| 0° F., dry | |
| 1 week, % vol. change | −1.03 |
| % wt. change | 0.0 |
| 180° F., dry | |
| 1 week, % vol. change | +1.83 |
| % wt. change | 0.0 |

EXAMPLE XVII

In a three-necked flask was placed 1,465 g. aniline (15.75 mols), 231 g. paraformaldehyde (7.0 mols HCHO) and 73 g. of Superfiltrol acid clay. The temperature was raised and water was removed in the interval 100° to 115° C. The temperature was further raised to 150° C. and held at that point for two hours. The catalyst was filtered from the product, and 374 g. unreacted aniline was recovered by distillation at a reduced pressure. The residue weighed 1,046 g. molecular weight 268, and contained 53.5 wt. % diamine.

EXAMPLE XVIII

Two hundred grams of the polyamine of Example XVII was dissolved in 1,400 g. of monochlorobenzene and added to a solution of 437 g. of phosgene dissolved in 1,600 g. of chlorobenzene at such a rate that the temperature was maintained in the range 25° to 30° C. The resulting slurry was then heated to 130° C. over a 2-hour period while passing in a slow stream of phosgene. Heating was continued at 130° C. for an additional hour. A total of 560 g. of phosgene was used. All excess phosgene was removed by sparging the solution with a stream of dry nitrogen. Solvent was removed by flash evaporation and the polyisocyanate residue was finished by stripping to a pot temperature of 150° C. at 2 mm. Hg pressure. The product weighed 247 g. Table 1 gives the properties of this polyisocyanate, which represents the product obtained before the improvement of the present invention.

EXAMPLE XIX

The experiment of Example XVII was repeated except a synthetic silica-alumina cracking catalyst, 15 mols of aniline and 6 mols of formaldehyde (as 37% formalin) were used. The product was converted to the polyisocyanate by the procedure of Example XVIII. The properties of this polyisocyanate given in Table 1 represent those of a product before the improvement of the present invention.

EXAMPLE XX

The experiment of Example XVII was repeated except a synthetic silica-alumina cracking catalyst, 15 mols of aniline and 6 mols of formaldehyde were used and after water was removed, the temperature was raised to 175° C. and the reaction product digested for 5 hours. The product was converted to the polyisocyanate by the procedure of Example XVIII and the properties given in Table 1 show the improvement in hydrolyzable chloride content over the polyisocyanates of Examples XVIII and XIX.

EXAMPLE XXI

In a 1-gallon, stainless-steel autoclave were placed 13.5 mols aniline, 6 mols formaldehyde (as paraformaldehyde) and 63 g. synthetic silica-alumina cracking catalyst. The autoclave was flushed with nitrogen, heated to 200° C. and held at that temperature for one hour. The autoclave was cooled, the product was removed and filtered to remove catalyst. Excess aniline was removed by distillation at reduced pressure, giving 939 g. polyamine. The product was converted to the polyisocyanate by the procedure of Example XVIII. The properties are given in Table 1.

TABLE 1

| EXAMPLE | XVIII | XIX | XX | XXI |
|---|---|---|---|---|
| Polyamine | | | | |
| Mols aniline/mol HCHO | 2.25 | 2.5 | 2.5 | 2.25 |
| Catalyst | Acid clay | Si-Al | Si-Al | Si-Al |
| Reaction temp., ° C. | 150 | 150 | 150 | 200 |
| Reaction time., hrs. | 2 | 2 | 2 | 1 |
| Digestive temp., ° C. | — | — | 175 | — |
| Digestive time., hrs. | — | — | 5 | — |
| % Diamine | 53.5 | 60 | 61 | 57 |
| Polyisocyanate | | | | |
| NCO, meq./g. | 7.50 | 7.64 | 7.72 | 7.38 |
| Hydrolyzable Cl, % | 6.04 | 3.0 | 0.41 | 1.02 |
| Viscosity, cps. 25° C. | 9,600 | 200 | 53 | 315 |
| Carbonyl (carbamoyl) 5.75μ | High | Very strong | Very weak | Fairly low |

EXAMPLE XXII

This example shows the further reduction of the hydrolyzable chlorine content achieved by adding the formaldehyde to the hot aniline and catalyst mixture rather than following a cold premixing procedure.

A mixture of 10.8 mols of aniline and 50 g. of synthetic silica-alumina cracking catalyst was placed in a stainless steel autoclave, flushed with nitrogen and heated to 200° C. Aqueous formalin (6 mols HCHO) was injected over a period of 1.3 hours. Heating was continued at 200° C. for 2 hours. The reaction mixture was cooled, removed from the autoclave and filtered to remove catalyst. Unreacted aniline was removed by distillation at reduced pressure and the polyamine residue weighed 1,023 grams. The product was phosgenated by the procedure given in Example XVIII. Table 2 shows the effectiveness of this technique in terms of decreased hydrolyzable chloride.

TABLE 2

| Polyamine | | Example XXII |
|---|---|---|
| Mixing procedure | Cold premixing | Hot addition |
| Aniline/HCHO | 1.8/1 | 1.8/1 |

TABLE 2-continued

| Polyamine | | Example XXII |
|---|---|---|
| Temperature, °C. | 200 | 200 |
| Time, hours | 2 | 2 |
| % Diamine | 41.4 | 34 |
| Polyisocyanate | | |
| NCO, meq./g. | 7.42 | 7.50 |
| Hydrolyzable Cl, % | 1.60 | 0.65 |
| Carbonyl, 5.75μ | Fairly strong | Low |

In Example XXIII is given a preferred embodiment of the practice of my invention wherein a two-step process is used to give higher polyamine suitable for conversion to polyisocyanate. The polyisocyanate thus produced has low hydrolyzable chloride content, low viscoity and is highly satisfactory for the commerical production of rigid polyurethane products.

EXAMPLE XXIII

In a 25-gallon, heated, stirred, stainless steel kettle equipped with a back pressure regulator was placed 100 lbs. of aniline and 2.2 lbs. of silica-alumina cracking catalyst under a nitrogen blanket. The temperature was raised to 140° C. and 43.6 lbs. of aqueous formaldehyde (37% HCHO) were added. The temperature was held a 140° C. for 1 hour and then raised to 200° C for 2 hours. The reaction mixture was cooled to 100° C., filter-aid was added, and the catalyst was removed by filtration. Water and excess aniline were removed by vacuum distillation. The residue weighed 71.5 lbs. A portion of the product was converted to the polyisocyanate by the phosgenation procedure described in Example XVIII.

In Table 3 are given the properties of the polyamine and derived polyisocyanate after the 140° C. heating stage and also after the 200° C. digestion stage to illustrate the improvement realized by the practice of the present invention.

TABLE 3

| Polyamine | Reaction Only | Reaction and Digestion |
|---|---|---|
| Aniline/formaldehyde ratio | 3.0 | 3.0 |
| Catalyst | Silica-alumina | Silica-alumina |
| Temperature, °C. | 140° for 1 hr. | 140° for 1 hr. then 200° for 2 hrs. |
| % Diamine | 51 | 65 |
| % 2,4'-Isomeric diamine | 19.4 | 28.8 |
| Polyisocyanate | | |
| NCO, meq./g. | 7.49 | 7.78 |
| Chloride, % | 3.68 | 0.70 |
| Viscosity, cps. 25° C. | 5,880 | 52.5 |

I claim:

1. A method for preparing a mixture of diaminodiphenylmethanes containing a predetermined percentage of 2,4'-isomers within the range of about 15 wt. % to about 90 wt. % which comprises the steps of:
   A. reacting about 1 to about 10 mols aniline per mol formaldehyde in the presence of a solid acidic siliceous catalyst at a first temperature within the range of about 80° to about 150° C. to thereby provide a reaction product comprising diaminodiphenylmethane isomers, secondary amines and higher molecular weight condensation products of aniline and formaldehyde;
   B. heating said mixture at a second temperature within the range of about 175° to about 250° C. for about 1 to about 5 hours to thereby convert said secondary amines to polyaminopolyphenylmethane compounds;
   C. recovering said diaminodiphenylmethane isomers and higher molecular weight condensation products from the reaction mixture;

whereby the predetermined percentage of 2,4'-isomers is formed by selecting at least one of said first temperature or said second temperature as being the temperature at which the predetermined percentage of 2,4'-isomer is formed.

2. The method of claim 1 wherein the solid acidic catalyst is an acid activated clay and wherein the temperature selected for determining the 2,4'-isomer concentration is said second temperature.

3. The method of claim 1 wherein said solid acidic catalyst is selected from the group consisting of silica-alumina catalysts and silica-magnesia catalysts and wherein the temperature selected for determining the 2,4'-isomer concentration is said first temperature.

4. The method of claim 1 wherein the solid acidic catalyst and aniline are preheated to the reaction temperature prior to reacting the aniline and formaldehyde.

5. In a process for producing a reaction product of aniline and formaldehyde which contains a diaminodiphenylmethane mixture together with a mixture of polymethylene polyphenylpolyamines having from two to four methylene groups, the method of obtaining between about 15wt. % and about 95 wt. % of 2,4'-diaminodiphenylmethane in said diaminodiphenylmethane mixture which comprises:
   A. heating an aniline-formaldehyde mixture containing from about one to about ten mols of aniline for each mol of formaldehyde;
   B. in the presence of a solid acidic siliceous catalyst of the group consisting of acid-activated siliceous clays and silica-alumina of silica-magnesia catalysts;
   C. at a reaction temperature within the range of about 80° to 300° C.; and
   D. controlling the proportion of 2,4'-diaminodiphenylmethane in the said reaction products by controlling the reaction temperature within said range when the catalyst is an acid-activated siliceous clay and by controlling the starting temperature of the reaction within said range when the catalyst is silica-alumina or silica-magnesia.

6. The method of claim 5 wherein comprises conducting the process of said claim and then,
   E. digesting the reaction product at a temperature of about 175° to about 200° C, in presence of the catalyst for about one to about five hours to convert secondary polyamine groups in the polyamines of the reaction prdouct to polymethylene polyphenylpolyamines.

7. In a process for producing a reaction poduct of aniline and formaldehyde which contains a diaminodiphenylmethane mixture together with a mixture of polymethylenepolyphenylpolyamines having from two to four methylene groups, the method of obtaining between about 15 and about 95 wt. % of 2,4'-diaminodiphenylmethane in said diaminodiphenylmethane mixture while avoiding the presence of secondary polyamines therein which comprises the steps of:
   A. reacting about 1 to about 10 mols aniline per mol formaldehyde in the presence of a solid acidic siliceous catalyst of the group consisting of acid-activated siliceous clays and silica-alumina of silica-magnesia catalysts at a first temperature within the range of about 80° to about 150° C. to thereby provide a reaction product comprising diaminodiphenylmethane isomers, secondary amines and higher molecular weight condensation products of aniline and formaldehyde;

B. heating said mixture at a second temperature within the range of about 175° to about 250° C. for about 1 to about 5 hours to thereby convert said secondary amines to polyaminopolyphenylmethane compounds;

C. controlling the proportion of 2,4'-diaminodiphenylmethane in said reaction products by controlling the temperature within the ranges of steps (A) or (B)] when the catalyst is an acid-activated siliceous clay and by controlling the starting temperature within the range of step (A) when the catalyst is silica-alumina or silica-magnesia; and D. recovering said diaminodiphenylmethane isomers and higher molecular weight condensation products from the reaction mixture.

8. In a process for producing a reaction product of aniline and formaldehyde which contains a diaminodiphenylmethane mixture together with a mixture of polymethylenepolyphenylpolyamines having from two to four methylene groups, the method of obtaining between about 30 and about 95 wt. % of 2,4'-diaminodiphenylmethane in said diaminodiphenylmethane mixture which comprises:

A. heating an aniline-formaldehyde mixture containing from about 1 to about 10 mols of free aniline for each mol of formaldehyde;

B. with an acid-activated siliceous clay catalyst;

C. at a reaction temperature within the range of about 80° to 250° C.; and

D. controlling the proportion of 2,4'-diaminodiphenylmethane in the said reaction products by controlling the reaction temperature within said range.

9. In a process for producing a reaction product of aniline and formaldehyde which contains a diaminodiphenylmethane mixture together with a mixture of polymethylenepolyphenylpolyamines having from two to four methylene groups, the method of obtaining between about 15 wt. % and about 50 wt. % of 2,4'-diaminodiphenylmethane in said diaminodiphenylmethane mixture which comprises:

A. heating an aniline-formaldehyde mixture containing from about 1 to about 10 mols of free aniline for each mol of formaldehyde;

B. with a silica-alumina or silica-magnesia catalyst;

C. at a reaction temperature within the range of about 80° to 250° C.; and

D. controlling the proportion of 2,4'-diaminodiphenylmethane in the said reaction products by controlling the starting temperature of the reaction within said range.

10. The method of claim 9 wherein the catalyst is a silica-alumina cracking catalyst.

11. The method of claim 9 wherein the catalyst and the aniline are preheated to the reaction temperature before the formaldehyde is admixed therewith.

12. A process for producing a reaction product of aniline and formaldehyde as defined in claim 5 wherein the reaction temperature is within the range of about 120° to about 200° C.

* * * * *